US005567417A

United States Patent [19]
Sasisekharan et al.

[11] Patent Number: 5,567,417
[45] Date of Patent: Oct. 22, 1996

[54] METHOD FOR INHIBITING ANGIOGENESIS USING HEPARINASE

[75] Inventors: Ramnath Sasisekharan, Arlington; Marsha A. Moses, Brookline; Matthew A. Nugent, Bedford; Charles L. Cooney, Brookline; Robert S. Langer, Newton, all of Mass.

[73] Assignees: Massachusetts Institute of Technology, Cambridge; Children's Medical Center Corporation, Boston, both of Mass.

[21] Appl. No.: 431,476

[22] Filed: May 1, 1995

Related U.S. Application Data

[63] Continuation of Ser. No. 153,873, Nov. 17, 1993, abandoned.
[51] Int. Cl.$^6$ ..................................................... A61K 38/51
[52] U.S. Cl. ........................................... 424/94.5; 435/232
[58] Field of Search ............................. 424/94.5; 435/232

[56] References Cited

FOREIGN PATENT DOCUMENTS

| | | |
|---|---|---|
| 0380370 | 8/1990 | European Pat. Off. . |
| 0394971 | 10/1990 | European Pat. Off. . |
| 8908456 | 9/1989 | WIPO . |
| 9102977 | 3/1991 | WIPO . |
| 9217203 | 10/1992 | WIPO . |

OTHER PUBLICATIONS

Vlodavsky et al., PNAS USA 84: 2292–2296 (Apr. 1987).
Folkman et al., Am J. Pathol. 130(2): 393–400 (Feb. 1988).
Bashkin et al., Biochemistry 28: 1737–1743 (1989).
Nakajima et al., J. of Biol. Chem 259(4): 2283–2290 (1984).
Auerback, et al., *J. Microvasc. Res.*, 29:401–411 (1985).
Ausprunk, D. H., et al., " Migration and Proliferation of Endothelial Cells in Preformed and Newly Formed Blood Vessels During Tumor Angiogenesis", *J. Microvasc. Res.*, 14:153–65 (1977).
Baird, A., et al., *N. Biochem. Biophy. Res. Commun.*, 142:428–435 (1987).
Bohmer, L. H., et al., "Purification and Characterization of a Novel Heparinase", *J. Biol. Chem.*, 265(23):13609–13617 (1990).
Casu, B., "Structure and Biological Activity of Heparin", *Adv. Carbohydr. Chem. Biochem.*, 43:51–134 (1985).
D'Amore, et al., "Endothelial Cell Mitogens Derived from Retina and Hypothalamus: Biochemical and Biological Similarities", *J. Cell Biol.*, 99:1545–1549 (1984).
Folkman, J. et al., "Minireview–Angiogenesis", *J. Biol. Chem.*, 267(16):10931–10934 (1992).
Folkman, J., et al., "A Heparin–Binding Angiogenic Protein–Basic Fibroblast Growth Factor–Is Stored Within Basement Membrane", *Am. J. Pathol.*, 130:393–400 (1988).
Folkman, J., et al., "Angiogenesis Inhibition and Tumor Regression Caused by Heparin or a Heparin Fragment in the Presence of Cortisone", *Science*, 221:719–725 (1983).

Folkman, J., et al., "Angiogenic Factors", *M. Science*, 235:442–447 (1987).
Folkman, J., "Tumor Angiogenesis", *Advances in Cancer Research*, Academic Press, Inc., New York, 43:175–203 (1985).
Folkman, J., et al., "Control of Angiogenesis With Synthetic Heparin Substitutes", *Science*, 243:1490–1493 (1989).
Galliher, P. M., et al., "Regulation of Heparinase Synthesis in *Flavobacterium Heparinum* ", *Eur. J. Appl. Micorbiol. Biotechnol.* 15:252–257 (1982).
Galliher, P. M. et al., "Heparinase Production by *Flavobacterium Heparinum* ", *Appl. Environ. Microbiol.*, 41(2):360–365 (1981).
Gitay–Goren, et al., "The Binding of Vascular Endothelial Growth Factor to Its Receptors is Dependent on Cell Surface–associated Herapin–like Molecules", *J. Biol. Chem.*, 267(9):6093–6098 (1992).
Gospodarowicz, D., et al., "Heparin Protects Basic and Acidic FGF From Inactivation", *J. Cell Physiol.*, 128:475–484 (1986).
Jacobson, I., et al., "Biosynthesis of Heparin (Concerted Action of Late Polymer–modification Reactions)", *J. Biol. Chem.* 255:5094–5100 (1980).
Kiefer, M. C., et al., "Ligand–affinity Cloning and Structure of a Cell Surface Heparan Sulfate Proteoglycan That Binds Basic Fibroblast Growth Factor", *Proc. Natl. Acad. Sci. USA*, 87:6985–6989 (1990).
Kurokawa, M., et al., "Neutralizing antibodies inhibit. . . ," *J. Biol. Chem.*, vol. 264, No. 13, pp. 7686–7691 (May 5, 1989).
Klagsbrun, M., et al., "A Dual Receptor System Is Required For Basic Fibroblast Growth Factor Activity", *Cell*, 67:229–231 (1991).
Lindahl, U., et al., "Biosynthesis of Heparin", *Trends Biochem. Sci.*, 11:221–225 (1986).
Lindahl, U., et al., "Biosynthesis of Heparin and Heparan Sulfate", *The Biology of Proteoglycans*, Academic Press, Inc., 59–104 (1987).
Lindblom, A., et al., "Domain Structure of Endothelial Heparan Sulphate", *Biochem J.*, 279:821–829 (1991).
Lindhardt, R. J., et al., "Search for the herapin Antithrombin III–binding Site Precursor", *J. Biol. Chem.*, 267:2380–2387 (1992).

(List continued on next page.)

Primary Examiner—Michael G. Wityshyn
Assistant Examiner—Jean C. Witz
Attorney, Agent, or Firm—Arnall Golden & Gregory

[57] ABSTRACT

Pharmaceutical compositions for delivering an effective dose to a desired site of a heparinase. These compositions are based on the discovery that heparinase alone can inhibit angiogenesis. The effective dosage is dependent not only on the heparinase, but also on the method and means of delivery, which can be localized or systemic. For example, in some applications, as in the treatment of psoriasis or diabetic retinopathy, the inhibitor is delivered in a topical ophthalmic carrier. In other applications, as in the treatment of solid tumors, the inhibitor is delivered by means of a biodegradable, polymeric implant.

14 Claims, 3 Drawing Sheets

OTHER PUBLICATIONS

Lindhardt, R. J., "Heparin: An Important Drug Enters Its Seventh Decade", *Chemistry & Industry*, 45–50 (1991).

Lobb, R. R., "Thrombin Inactivates Acidic Fibroblast Growth Factor but Not Basic Fibroblast Growth Factor", *Biochem.*, 27:2572–2578 (1988).

Mignatti, P., et al., "Tumor Invasion Through the Human Amniotic Membrane; Requirement for a Proteinase Cascade", *Cell*, 47:487–498 (1986).

Moscatelli, D., "High and Low Affinity Binding Sites for Basic Fibroblast Growth Factor on Cultures Cells: Absence of a Role for Low Affinity Binding in the Stimulation of Plasminogen Activator Production by Bovine Capillary Endothelial Cells", *J. Cell. Physiol.*, 131:123–130 (1987).

Nader, H. B., et al., "Heparin Sequences in the Heparan Sulfate Chains of an Endothelial Cell Proteoglycan", *Proc. Natl. Acad. Sci. USA*, 84:3565–3569 (1987).

Nakamura, et al., "Purification and Properties of *Bacteroides Heparinolyticus* Heparinase (Heparin Lyase, EC 4.2.2.7)", *J. Clin. Microbiol.*, 26(5):1070–1071 (1988).

Nugent, M. A., et al., "Kinetics of Basic Fibroblast Growth Factor Binding to Its Receptor and heparan Sulfate Proteoglycan: A Mechanism for Cooperativity", *Biochemistry*, 31(37):8876–8883 (1992).

Patz, A., "Clinical and Experimental Studies on Retinal Neovascularization", *Am. J. Opthalmol.*, 94:715–743 (1982).

Payza, A. N., et al., "Bacterial Degradation of Heparin", *Nature*, 177:88–89 (1956).

Bashkin, P., et al., "Basic fibroblast growth factor. . . ," Biochem., 28, No. 4, pp. 1737–1743 (Feb. 21, 1989).

Rapraeger, A. C., et al., "Requirement of heparan Sulfate for bFGF–Mediated Fibroblast Growth and Myoblast Differentiation", *Science*, 252:1705–1708 (1991).

Rifkin, D. B., et al., "The Involvement of Proteases and Protease Inhibitors in Neovascularization", *Acta Biol. Med. Germ.*, 40:1259–1263 (1981).

Rosengart, T. K., et al., "Heparin Protects Heparin–Binding Growth Factor–I From Proteolytic Inactivation In Vitro ", *Biochem. Biophys. Res. Commun.*, 152:432–440 (1988).

Sasisekharan, R., et al., "Cloning and Expression of Heparinase I Gene from *Flavobacterium Heparinum*", *Proc. Natl. Acad. Sci. USA*, 90:3660–3664 (1993).

Salvers, A. A., et al., "Fermentation of Mucin and Plant Polysaccharides by Strains of *Bacteroides* from the Human Colon", *Appl. Environ. Microbiol.*, 33(2):319–322 (1977).

Schreiber, A. B., et al., "Interaction of Endothelial Cell Growth Factor with Heparin: Characterization by Receptor and Antibody Recognition", *Proc. Natl. Acad. Sci. USA*, 82:6138–6142 (1985).

Shing, Y., et al., "Heparin Affinity: Purification of a Tumor––Derived Capillary Endothelial Cell Growth Factor", *Science*, 223:1296–1299.

Taylor, S., et al., "Protamine is an Inhibitor of Angiogenesis", *Nature (London)*, 297:307–312 (1982).

Thornton, S. C., et al., "Human Endothelial Cells: Use of Heparin in Cloning and Long–Term Serial Cultivation", *Science*, 222:623–625 (1983).

Turnbull, J. E., et al., "Identification of the Basic Fibroblast Growth Factor Binding Sequence in Fibroblast Heparan Sulfate", *J. Biol. Chem.*, 267(15):10337–10341 (1992).

Vlodavsky, I., et al., "Endothelial Cell–derived Basic Fibroblast Growth Factor: Synthesis and Deposition Into Subendothelial Extracellular Matrix", *Proc. Natl. Acad. Sci. USA*, 84:2292–2296 (1987).

Vlodavsky, I., et al., "Extracellular Matrix–resident Growth Factors and Enzymes: Possible Involvement in Tumor Metastasis and Angiogenesis", *Cancer and Metastasis Reviews*, 9:203–226 (1990).

Yang, V. C., et al., "Purification and Characterization of heparinase from *Flavobacterium Heparinum*", *J. Biol. Chem.*, 260:1849–1857 (1987).

Yavon, A., et al., "Cell Surface, heparin–like Molecules Are Required for Binding of Basic Fibroblast Growth Factor to Its High Affinity Receptor", *Cell*, 64:841–848 (1991).

Zimmermann, J. F., et al., "The Release of heparinase from the Periplasmic Space of *Flavobacterium Heparinum* by Three–Step Osmotic Shock", *Appl. Biochem. Biotech.*, 30:137–148) (1991).

METHOD FOR INHIBITING ANGIOGENESIS USING HEPARINASE

The United States government has rights in this invention by virtue of National Institutes of Health GM25810 to Robert S. Langer and a National Science Foundation grant to Charles Cooney.

This is a continuation of application U.S. Ser. No. 08/153,873 filed on Nov. 17, 1993, now abandoned.

BACKGROUND OF THE INVENTION

Angiogenesis is a fundamental process by which new blood vessels are formed, as reviewed, for example, by Folkman and Shing, *J. Biol. Chem.* 267 (16), 10931–10934 (1992). It is essential in reproduction, development and wound repair. Under these conditions, angiogenesis is highly regulated, so that it is turned on only as necessary, usually for brief periods of days, then completely inhibited. However, many diseases are driven by persistent unregulated angiogenesis. In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

Capillary blood vessels consist of endothelial cells and pericytes. These two cell types carry all of the genetic information to form tubes, branches and whole capillary networks. Specific angiogenic molecules can initiate this process. Specific inhibitory molecules can stop it. These molecules with opposing function appear to be continuously acting in concert to maintain a stable microvasculature in which endothelial cell turnover is thousands of days. However, the same endothelial cells can undergo rapid proliferation, i.e. less than five days, during burst of angiogenesis, for example, during wound healing.

A number of proteases have been implicated as key factors in angiogenesis. See, for example, Mignatti, et al., *Cell* 47, 487–498 (1986) and Rifkin, et al., *Acta. Biol. Med. Germ.* 40, 1259–1263 (1981), who suggest several enzymes in a proteolytic cascade, including plasminogen activator and collagenase, must be inhibited in order to inhibit angiogenesis.

Under normal conditions, angiogenesis is associated with such events as wound healing, corpus luteum formation and embryonic development, as discussed by Folkman, et al., *Science* 43, 1490–1493 (1989). However, a number of serious diseases are also dominated by abnormal neovascularization including solid tumor growth and metastases, some types of eye disorders, and rheumatoid arthritis, reviewed by Auerbach, et al., *J. Microvasc. Res.* 29, 401–411 (1985); Folkman, *Advances in Cancer Research*, eds. Klein and Weinhouse, pp. 175–203 (Academic Press, New York 1985); Patz, *Am. J. Opthalmol.* 94, 715–743 (1982); and Folkman, et al., *Science* 221, 719–725 (1983). For example, there are a number of eye diseases, many of which lead to blindness, in which ocular neovascularization occurs in response to the diseased state. These ocular disorders include diabetic retinopathy, neovascular glaucoma, inflammatory diseases and ocular tumors (e.g. retinoblastoma). There are a number of other eye diseases which are also associated with neovascularization, including retrolental fibroplasia, uveitis, approximately twenty eye diseases associated with choroidal neovascularization and approximately forty eye diseases which are associated with iris neovascularization. The current treatment of these diseases is inadequate, especially once neovascularization has occurred, and blindness often results.

Key components of the angiogenic process are the degradation of the basement membrane, the migration and proliferation of capillary endothelial cell (EC) and the formation of three dimensional capillary tubes. The normal vascular turnover is rather low: the doubling time for capillary endothelium is from 50–20,000 days, but it is 2–13 days for tumor capillary endothelium. The current understanding of the sequence of events leading to angiogenesis is that a cytokine capable of stimulating endothelial cell proliferation, such as fibroblast growth factor (FGF), causes release of collagenase or plasminogen activator which, in turn, degrade the basement membrane of the parent venule to facilitate in the migration of the endothelial cells. These capillary cells, having 'sprouted' from the parent vessel, proliferate in response to growth factors and angiogenic agents in the surrounding to form lumen and eventually new blood vessels. Thus, inhibition of angiogenesis can occur at any of the above key junctures. A chemical agent which prevents the continued spread of vascularization could have broad applicability as a therapy for those disease in which neovascularization plays a prominent role.

Heparin and heparan sulfate represent a class of glycosaminoglycans characterized by a linear polysaccharide of D-glucosamine (1→) linked to hexuronic acid (Linhardt, R. J. (1991) Chem. Ind. 2, 45–50; Casu, B. (1985) Adv. Carbohydr. Chem. Biochem. 43, 51–134). Heparin and heparan sulfate are complex carbohydrates that play an important functional role in the extracellular matrix of mammals. These polysaccharides modulate and regulate tissue level events that take place either during development under normal situations or wound healing and tumor metastasis under pathological conditions.

Much of the current understanding of heparin and heparan sulfate sequence has relied on studies of their biosynthesis (Linhardt, R. J., Wang, H. M., Loganathan, D., and Bae, J. H. (1992) Biol. Chem. 267, 2380–2387; Lindahl, U., Feingold, D., and Roden, L. (1986) Trends Biochem. Sci. 11, 221–225; Jacobson, I., and Lindahl U. (1980) J. Biol. Chem. 255, 5094–5100; Lindahl, U., and Kjellen, L. (1987) in The Biology of Extracellular Matrix Proteoglycans (Wight, T. N., and Mecham R., eds) pp. 59–104, Academic Press, New York).

Heparan sulfate, which is chemically almost indistinguishable from heparin, is believed to be present on virtually all cell surfaces. Heparin-like molecules are associated with membrane proteins and are called proteoglycans. Proteoglycans are predominantly found in the extracellular matrix (ECM) and function in cell adhesion to the extracellular matrix. It is increasingly recognized that heparin is more than a mere structural oligosaccharide as it interacts with other key proteins of the extracellular matrix, such as laminin, fibronectin and collagen, and helps to define the physiological properties of the matrix. Heparin interacts with an array of cytokine-like growth factors present in the extracellular matrix, by facilitating their biochemical interaction with receptors and by protecting them from proteolytic degradation. Heparin potentiates the biological activity of aFGF, as reported by Thornton, et al., *Science* 222, 623–625 (1983), possibly by potentiating the affinity of aFGF for its cell surface receptors, as reported by Schreiber, et al., *Proc. Natl. Acad. Sci. USA* 82, 6138–6142 (1985). Heparin protects aFGF and bFGF from degradation by heat, acid and proteases, as reported by Gospodarowicz and Cheng, *J. Cell Physiol.* 128, 475–4 84 (1986); Rosengart, et al., *Biochem. Biophys. Res. Commun.* 152, 432–440 (1988); and Lobb *Biochem.* 27, 2572–2578 (1988). bFGF is stored in the extracellular matrix and can be mobilized in a biologically active form by heparin or heparan sulfate, as reported by Vlodavsky, et al., *Proc. Natl. Acad. Sci. USA* 84, 2292–2296 (1987) and Folkman, et al., *Am. J. Pathol.* 130, 393–400 (1988). The binding of FGF to heparan sulfate is a prerequisite for the binding of FGF to its high affinity receptor on the cell surface, as reported by Yayon, et al., *Cell* 64, 841–848 (1991) and Papraeger, et al., *Science* 252, 1705–1708 (1991). A specific heparan sulfate proteoglycan has been found to mediate the binding of bFGF to the cell surface, as described by Kiefer, et al., *Proc. Natl. Acad. Sci. USA* 87, 6985–6989 (1990).

Although a number of these studies have focused on the role of heparin-like molecules in neovascularization, little is known about the role of heparin-degrading enzymes in neovascularization. Heparin-like molecules such as heparin and heparan sulfate bind several cytokines, which are angiogenic, and modulate their function either by stabilizing them or by controlling their bioavailability, as reported by Folkman and Shing, *J. Biol. Chem.* 267, 10931–10934 (1992). These molecules have been shown by Klagsbrun and Baird *Cell* 67, 229–231 (1991), to act as low affinity receptors on cell surfaces and to facilitate growth factor activity and receptor binding.

These observations suggest that enzymes which degrade heparin-like molecules can play a role in modulating neovascularization. Far less is known about the direct role of heparinase on the angiogenic process than is known about that of its substrate, heparin.

Heparin lyases are a general class of enzymes that are capable of specifically cleaving the major glycosidic linkages in heparin and heparan sulfate. Three heparin lyases have been identified in Flavobacterium heparinum, a heparin-utilizing organism that also produces exoglycouronidases, sulfoesterases, and sulfamidases that further act on the lyase-generated oligosaccharide products (Yang, et al. *J. Biol. Chem.* 260, 1849–1857 (1987); Galliher, et al. *Eur. J. Appl. Microbiol.* Biotechnol. 15, 252–257 (1982). These lyases are designated as heparin lyase I (heparinase, EC 4.2.2.7), heparin lyase II (heparinase II, no EC number) and heparin lyase III (heparitinase EC 4.2.2.8). The three purified heparin lyases differ in their capacity to cleave heparin and heparan sulfate: Heparin lyase I primarily cleaves heparin, heparin lyase III specifically cleaves heparan sulfate and heparin lyase II acts equally on both heparin and heparan. Several Bacteroides sp. (Saylers, et al. Appl. *Environ. Microbiol.* 33, 319–322 (1977); Nakamura, et al. *J. Clin. Microbiol.* 26, 1070–1071 (1988)) also produce heparinases. A heparinase has also been purified to apparent homogeneity from an unidentified soil bacterium by Bohmer, et al. *J. Biol. Chem.* 265, 13609–13617 (1990).

The in vivo effect of these heparinases, other than on the degradation of heparin, has never been determined.

It is an object of the present invention to provide pharmaceutical compositions, and method of use thereof, based on heparinases, for the treatment of diseases involving abnormal angiogenesis.

It is a further object of the present invention to provide pharmaceutical compositions, and method of use thereof, based on heparinases, for inhibition of capillary endothelial cell proliferation and migration.

It is another object of the present invention to provide topical and controlled release pharmaceutical compositions, and methods of use thereof, based on heparinases, for inhibition of angiogenesis.

SUMMARY OF THE INVENTION

Pharmaceutical compositions for delivering an effective dose of a heparinase to a desired site. These compositions are based on the discovery that heparinase alone can inhibit angiogenesis. The heparin-degrading enzymes heparinases I and III have now been demonstrated to inhibit both neovascularization in vivo and proliferation of capillary endothelial cells mediated by basic fibroblast growth factor in vitro, and caused dramatic loss in binding of basic fibroblast growth factor to these cells. Heparinase II did not inhibit neovascularization in vivo, had marginal effect on endothelial cell proliferation and the binding of basic fibroblast growth factor to these cells, but is very useful in the alteration of smooth muscle cell proliferation.

The effective dosage for inhibition of angiogenesis in vivo, defined as inhibition of capillary endothelial cell proliferation and migration and blood vessel ingrowth, is extrapolated from in vitro inhibition assays. In vitro assays have been developed to screen for inhibition of angiogenesis. Events that are tested include proteolytic degradation of extracellular matrix and/or basement membrane; proliferation of endothelial cells, migration of endothelial cells, and capillary tube formation. Effective dosages range from 10 nM to 100 nM heparinase I or III for inhibition of capillary endothelial cell proliferation and between 1 μg and 4 μg heparinase I or III for inhibition of localized angiogenesis. The effective dosage is dependent not only on the heparinase, but also on the method and means of delivery, which can be localized or systemic. For example, in some applications, as in the treatment of psoriasis or diabetic retinopathy, the inhibitor is delivered in a topical ophthalmic carrier. In other applications, as in the treatment of solid tumors, the inhibitor is delivered by means of a biodegradable, polymeric implant.

BRIEF DESCRIPTION OF THE DRAWINGS

FIGS. 1a, 1b, 1c and 1d are micrographs showing inhibition of angiogenesis by heparinase in the chick chronic membrane assay.

DETAILED DESCRIPTION OF THE INVENTION

It has been discovered that heparinases directly inhibit neovascularization. It has also been observed that heparinases of different substrate specificity differentially affect BCE proliferation and bFGF binding to these cells. For example, the substrate specificities of heparinases I, II and III from *F. heparinum* may control either the availability or the removal of unique heparin fragments essential for neovascularization. Heparinase III acts at the more "heparan sulfate-like regions" of the endothelial cell polysaccharide, leaving behind intact bFGF binding sites, and heparinase I cleaves the "heparin-like regions" of the polysaccharide containing the bFGF binding sites; thus both enzymes differentially modulate the availability of specific bFGF binding sites required for bFGF-mediated BCE proliferation, as described by Nader, et al. *Proc. Natl. Acad. Sci. U.S.A.* 84, 3565–3569 (1987); Lindblom, et al. *Biochem J.* 279, 821–829 (1991); and Turnbull, et al. *J. Biol. Chem.* 267, 10337–10341 (1992). However, since heparinase II non-specifically cleaves the polysaccharide primarily into disaccharides, this enzyme probably does not hit enough sites to alter heparan sulfate structure significantly enough to affect bFGF binding and activity.

In complete contrast to the observations described herein, it has been suggested by Folkman, J. & Shing, Y. *J. Biol. Chem.* 267, 10931–10934 (1992), that enzymes such as heparinases, which degrade ECM structural components, have a role in aiding the release of growth factors sequestered in the matrix and facilitating EC proliferation and neovascularization in vivo. For example, it has been proposed by Vlodavsky, et al. *Cancer Met. Rev.* 9, 203–226 (1990), that heparinases degrade the basement membrane serving as a reservoir for bFGF to initiate tumor or wound neovascularization.

As described herein, however, these enzymes appear to have another role wherein they inhibit neovascularization by depleting the low affinity receptors that are critical for bFGF mediated proliferation of endothelial cells and hence neovascularization. In addition to bFGF, several endothelial cell cytokines have been found by Gitay-Goren, et al. *J. Biol. Chem.* 267, 6093–6098 (1992) and Folkman, J. & Klagsbrun, M. *Science* 235, 442–447 (1987), to bind and be modulated by heparin-like molecules; thus heparinases could act on wide spectrum of heparin-dependent angiogenic factors. The mechanism described here for specific heparinase-mediated inhibition of bFGF binding and activity on BCEs is believed to be reflective of a general system for the control of capillary endothelial cell proliferation and neovascularization and therefore subject to regulation using any molecule having heparinase-like activity.

I. Heparinases (heparin lyases)

Sources of Heparinase

A variety of heparinases are produced in bacteria, especially *Flavobacterium heparinum*, which produces three distinct heparinases, heparinase I, heparinase II, and heparinase III. As described herein, heparinase I and heparinase III are potent inhibitors of neovascularization. In the preferred embodiment, only heparinase purified of other activities or contaminants is used. Although heparinase is commercially available, it is preferred to use a more highly purified form, especially when derived from *F. heparinum*, since the bacteria produces a number of enzymes other than heparinase, such as chondroitinase, as well as the three very different forms of heparinase. Reports of studies conducted with the commercially available forms of heparinase have contained conflicting results and non-reproducible data, presumably due to contamination with other materials.

As used herein, "heparinase" includes the enzymes derived from natural sources, as well as those which have been modified naturally or synthetically to alter their binding affinity and/or catalytic activity.

Purification, composition and specificity of Heparinase

I, II, AND III from *Flavobacterium heparinum*

Heparin lyase I (heparinase, EC 4.2.2.7), heparin lyase II (no EC number), and heparin lyase III (heparitinase, EC 4.2.2.8) have molecular weights (by sodium dodecyl sulfate-polyacrylamide gel electrophoresis) and isoelectric points (by isoelectric focusing) of $M_r$ 42,800, pI 9.1–9.2, $M_r$ 70,800, pI 9.9–10.1, respectively.

A method for purification is described below.

Materials

Enzyme assays and absorbance measurements were done on a UV 160 spectrophotometer from Shimadzu connected to a Fisher Scientific Isotamp model 9100 refrigerated circulating water bath. Fermentations were performed in a two-liter stirred tank fermenter from Applikon. Centrifugation was done on a Sorvall RC-5 refrigerated centrifuge in a GSA rotor from Du Pont. HPLC was performed using a LDC Milton-Roy Constametric IIIG pump, a Rheodyne 7125 injector, a Jule Linear Gradient Former, and an ISCO model UA-5 absorbance monitor with a 280-nm filter. The hydroxylapatite HPLC column 1×30 cm connected in series with a 1×5 cm guard column was from Regis, the Mono-S FPLC column was from Pharmacia LKB Biotechnology Inc., the $C_{18}$ column was from Vydac, and the Bio-Sil gel permeation HPLC column was from Bio-Rad. The capillary zone electrophoresis system and the silica capillaries were from Dionex. The Mini-Protein II electrophoresis chamber, a model 1405 horizontal electrophoresis cell, and a model 1420B power source were from Bio-Rad. The tube gel electrophoresis equipment was from E-C Apparatus Corp. The precast agarose IEF gels were from Iso-labs, and the prestained molecular weight markers and the Rapid Coomassie™ stain were from Diversified Biotech. The Bio-Gel HT hydroxylapatite was from Bio-Rad and the QAE-Sephadex was from Sigma. Pressure filtration units and 25- and 43-mm PM-10 filters were from Amicon. Heparin (porcine mucosal sodium salt) was from Celsus, heparan sulfate, dermatan sulfate, and chondroitin sulfate A, C, D, and E were from Seikagaku. Bovine serum albumin, lactose, protamine (free base), bromphenol blue, naphthol red, cytochrome c (bovine heart type VA), hyaluronic acid, CAPS, bis-Tris, HEPES, TES, dithiothreitol, MOPS, mercaptoethanol, iodoacetamide, and trypsin were for Sigma. The Coomassie reagent for the protein assay was from Bio-Rad. All water used in reagents was deionized and distilled in glass.

Assay

The spectrophotometer was adjusted to the optimum temperature of the particular lyase being assayed. A 700 μl quartz microcuvette containing 400 μg of substrate in 50 mM sodium phosphate buffer (containing 100 mM sodium chloride for heparin lyase I) was thermally equilibrated. A measured quantity of lyase was added, bringing the final volume to 400 μl and the cuvette was gently mixed. The microcuvette was then immediately returned to the spectrophotometer and the change of absorbance at 232 nm was measured at 10 seconds intervals over 3 min. The activity was measured from the change of absorbance/unit time using an extinction coefficient of 3800 $M^{-1}$ for products. The specific activity was then calculated by dividing the micromoles of product produced per minute by the milligrams of protein in the cuvette. The molecular weights used for heparin, heparan sulfate, and the chondroitin sulfates were 14,000, 20,000 and 25,000, respectively. Protein concentration was measured by the Bradford assay based on a bovine serum albumin standard curve.

Fermentation and Enzyme Recovery

*F. heparinum* (Payza, A. N., and Korn, E. D. (1956) *Nature* 77, 88–89) (ATCC 13, 125) was stored at −70° C. in a defined medium containing dimethyl sulfoxide (Me$_2$SO) (Zimmermann, J. J., Oddie, K., Langer, R., and Cooney, C. L. (1991) *Appl. Biochem. Biotech.* 30, 137–148). The organism was grown in a two liter stirred tank fermenter on heparin as the sole carbon source in defined medium by the method of Galliher, P. M., Cooney, C. L., Langer, R. S., and Linhardt, R. J. (1981) *Appl. Environ. Microbiol.* 41, 360–365). From 5 liters of fermentation broth, an 80 g wet cell pellet was obtained by centrifugation for 15 min at 12,000× g at 4° C. This pellet was suspended in 500 ml of 10 mM sodium phosphate buffer at pH 7.0 and 4° C. Cell suspension (20 ml at a time) was placed into a 50-ml stainless steel cup and sonicated with cooling for 10 min at 100 watts using a 40% pulsed mode. The disrupted cells were centrifuged at 12,500× g for 30 min at 4° C. and the pellet discarded. The 500 ml of supernatant, obtained by sonication and centrifugation, contained 16.3 mg/ml protein. Protamine free base (2.0 g) was dissolved in 20 ml of 10 mM sodium phosphate buffer, pH 7.0, and added dropwise with stirring to the 500 ml of supernatant. Centrifugation at 10,000× ×g, at 4° C. for 20 min, removed the precipitated DNA and gave 510 ml of supernatant.

Electrophoresis

Materials

Electrophoresis was performed using a Mini-Protean II electrophoresis cell from Bio-Rad (Richmond, Calif., U.S.A.). Acrylamide and N,N'-methylene bisacrylamide were from International Biotechnologies Inc. (New Haven, Conn., U.S.A.) or used as a prepared 40% acrylamide solution that is 37.5 acrylamide:1 N,N'-methylene bisacrylamide (Fischer Scientific, Fairlawn, N.J., U.S.A.). Tris {hydroxymethyl} aminomethane (Tris) was from Bio-Rad (Richmond, Calif., U.S.A.). N,N,N',N'- Tetramethylethylenediamine (TEMED) was from Boehringer Mannheim Biochemicals (Indianapolis, Ind., U.S.A.). Ammonium persulfate (APS) and glacial acetic acid were from Mallinckrodt Inc. (Pads, Ky., U.S.A.). Urea and glycerol were from Fisher Scientific (Fair Lawn, N.J., U.S.A.). Sodium dodecyl sulfate (SDS) was from BDH Chemicals, Ltd. (Poole, England). Naphthol red was from Sigma Chemical Co. (St. Louis, Mo., U.S.A.). 2-β-mercaptoethanol was from EM Science (Gibbstown, N.J., U.S.A.). Bromophenol blue was from MCB Manufacturing Chemists, Inc. (Cincinnati, Ohio, U.S.A.). Molecular Weight Standards and Rapid Coomassie Stain were from Diversified Biotech (Newton Centre, Mass., U.S.A.)

SDS-polyacrylamide gel electrophoresis (PAGE)

Separating gels (12% acrylamide, 10% SDS) were prepared by mixing 4.35 mL distilled water, 2.5 mL of 1.5M Tris, pH 8.8 and 3.0 mL of a commercially prepared solution of 37.5 acrylamide:1 N,N'-methylene bisacrylamide (Fischer Scientific, Fairlawn, N.J., U.S.A.) as described above. This solution was degassed under vacuum for at least 15 minutes. Next, 50 µL of APS (10%) and 5 µL of TEMED were added to the monomer solution to initiate polymerization. The gel solution was quickly poured between two glass plates separated by 0.75 mm spacers, overlaid with distilled water saturated gamma-butanol and allowed to polymerize at 25° C. for 60 minutes.

Stacking gel was prepared by mixing 6.4 mL distilled water, 2.5 mL 0.5M Tris, pH 6.8, 1.0 mL acrylamide/Bis solution (Fischer Scientific), 50 µL APS (10%) and 10 µL TEMED. The gamma-butanol was removed from the separating gel, the gel was rinsed with distilled water and the stacking gel solution was carefully added to the top of the separating gel. A well-forming electrophoresis comb was inserted in the stacking gel prior to polymerization. The stacking gel was allowed to polymerize for 60 minutes and the well-forming comb was removed just prior to loading of the samples.

Sample buffer was prepared by mixing 4.0 mL distilled water, 1.0 mL 0.5M Tris, pH 6.8, 0.8 mL glycerol, 1.6 mL SDS (10%), 0.4 mL 2- β-mercaptoethanol and 0.2 mL bromophenol blue (0.05% W/V). Samples and molecular weight standard markers for electrophoresis were diluted 1:4 in sample buffer and heated for 4 minutes at 100° C. just prior to loading into the wells formed earlier in the stacking gel. Running buffer (0.125M Tris, 1.0M glycine, 0.5% SDS, pH 8.3) was carefully overlaid on the stacking gel and the electrophoresis was conducted at a constant voltage of 200 V until the bromophenol blue marker moved to within 0.3 cm of the bottom of the gel (typically about 45 minutes). Following electrophoresis, the gels were either electrotransferred to nitrocellulose membranes or were stained with Rapid Coomassie Stain for 45 minutes followed by destaining with a 7.5% methanol/5% acetic acid solution.

Purification of heparin Lyases from *F. heparinum*

Batch Hydroxylapatite Adsorption and Release

The 510 ml of supernatant containing 15.6 mg/ml protein, used directly without freezing, was divided equally into four 250 ml polypropylene centrifuge containers and placed in an ice bath. Dry hydroxylapatite (HA) (20 g) was added to each container, gently stirred, lightly compacted by centrifugation at 1000× g for 2 min at 4° C., and the supernatant was decanted away from the HA matrix. The HA-bound protein was then resuspended in buffers having increasing concentrations of sodium phosphate and sodium chloride and recompacted by centrifugation. The supernatants were again decanted away from the matrix and assayed for enzyme activity and protein concentration. The buffers used to wash the HA matrix were prepared by mixing a solution of 10 mM sodium phosphate buffer at pH 6.8, with a solution of 250 mM sodium phosphate buffer at pH 6.8, containing 500 mM sodium chloride in ratios of 6:0, 5:1, 4:2, 3:3, 2:4, and 0:6 (v/v) at 4° C. The protein supernatant solutions were placed in dialysis tubing having a molecular weight cut-off of 14,000 and dialyzed overnight at 4° C. against 50 mM sodium phosphate buffer at pH 7.0.

QAE-Sephadex Chromatography

Lyase activity purified by batch HA was used immediately without freezing. A quaternary ammonium ethyl (QAE)-Sephadex chromatography step was performed at 4° C. Three batch HA-purified fractions (4:2; 3:3, and 2:4), having a total volume of 1.5 liters, containing more than 89% of the activity toward heparin and 88% of the activity toward heparan sulfate were consolidated (1.81 mg/ml protein and 1.72 units/ml toward heparin and 2.16 units/ml toward heparan sulfate) and applied directly in equal portions to three columns (2.5×20 cm) containing 600 ml of QAE-Sephadex. The QAE-Sephadex columns had been previously equilibrated with 50 mM sodium phosphate buffer, pH 7.0, at 4° C. Each column was then washed with 1-column volume of 50 mM phosphate buffer, pH 7.0, at 4° C. The fractions containing lyase activity that passed through the columns without interaction were collected and combined. The 2.6 liters of eluent was then concentrated to 63 ml (containing 8.23 mg/ml of protein) by Amicon pressure filtration at 60 psi and 4° C. using a 43 mm PM-10 membrane (10,000 molecular weight cut-off).

Hydroxylapatite HPLC

The 63 ml of QAE-Sephadex-purified and concentrated solution was divided into twelve 5 ml aliquots and stored at −70° C until needed. A 5 ml sample (43 mg of protein) was removed from the freezer, allowed to thaw at room temperature, and, using a 5 ml loop, injected onto a HA HPLC column. The HA-HPLC column had been equilibrated with 50 mM sodium phosphate buffer, pH 7.0. After loading the sample, the column was washed with 50 mM sodium phosphate buffer, pH 7.0, at 0.5 ml/min, for 20 min. A 60 ml linear gradient, from 50 mM sodium phosphate, pH 7.0, to 50 mM sodium phosphate buffer containing 750 mM sodium chloride, pH 7.0, was used to elute the column. The elution was monitored continuously at 280 nm. After the gradient was complete, the column was washed with 5.0 ml of 50 mM sodium phosphate containing 1M sodium chloride, pH 7.0, to remove tightly bound proteins, and then re-equilibrated with the 50 mM sodium phosphate buffer, pH 7.0. This fractionation step was repeated with the 11 remaining aliquots. The fractions corresponding to heparin lyase I, heparin lyase II, and heparin lyase III from each of the 12 fractionations were pooled, dialyzed against 20 volumes of 50 mM sodium phosphate buffer, pH 7.0, for 12 h at 4° C., and concentrated at 60 psi and 4° C. using Amicon pressure filtration equipped with PM-10 membranes. The three lyase preparations were each divided into 1-ml aliquots and frozen at −70° C.

Mono-S FPLC of heparin Lyases I and III

The concentrated heparin lyase I and heparin lyase III preparations, isolated from HA-HPLC, were taken from the −70° C. freezer, thawed at room temperature, and applied to a Mono-S FPLC HR 5/5 cation-exchange column equilibrated with 50 mM sodium phosphate buffer, pH 7.0. A portion of each lyase preparation, 350 µl containing 1.75 mg of protein, was injected and the column washed at 1 ml/min for 5 min with 50 mM sodium phosphate buffer, pH 7.0, to elute non-interacting proteins. A linear gradient from 50 mM sodium phosphate buffer, pH 7.0, to 50 mM sodium phosphate containing 500 mM sodium chloride, pH 7.0, was used and the elution was monitored at 280 nm. The active heparin lyase I and heparin lyase III fractions were dialyzed at 4° C. against 200 mM sodium phosphate buffer, pH 7.0, for 12 h and concentrated using Amicon Pressure Filtration with a PM-10 membrane (molecular weight cut-off 10,000).

Gel Permeation HPLC

The heparin lyase I and III preparation obtained from Mono-S FPLC and the heparin lyase II preparation obtained from HA-HPLC were applied to a Bio-Sil gel permeation chromatography (GPC) HPLC column (1×25 cm) that had been equilibrated with 200 mM sodium phosphate buffer, pH 7.0. Each lyase was injected (250 µl samples containing 800 µg of protein for heparin lyases I and III; 200 µl samples containing 1.5 mg of protein for heparin lyase II), eluted at a flow rate of 1 ml/min and absorbance at 280 nm was measured. This separation was repeated five times for heparin lyases I, II, and III. The active fractions were pooled together and assayed for lyase activity and protein concentration. Each heparin lyase was dialyzed against 50 mM sodium phosphate buffer, pH 7.0, concentrated at 60 psi and 4° C. using pressure filtration with 25 mm PM-10 membranes (molecular weight cut-off 10,000), and subdivided into 10 µl aliquots and stored at −70° C.

Characterization of the Three heparin Lyases

Assessment of Purity by Electrophoresis

Discontinuous SDS-PAGE was performed on the three heparin lyases using a modification of a procedure previously described by Laemmli. The gels were fixed with 12% (w/v) trichloroacetic acid, rinsed with deionized, distilled water and stained with a Rapid Coomassie Stain solution, and destained.

IEF gel electrophoresis was run on pre-cast agarose gels (85×100 mm). Two electrode wicks were wetted with 1 M phosphoric acid (anolyte) and 1M sodium hydroxide (catholyte). Electrophoresis was at 5 watts for 5 min, then at 10 watts for 1 h until the voltage was constant at 1200 V. The gel was immediately fixed in 15% aqueous trichloroacetic acid, blotted and rinsed with water, dried overnight, stained by using Coomassie G-250, and destained.

Continuous acid-urea gel electrophoresis was performed in 10% polyacrylamide tube gels. Heparin lyase I-III samples (10 µg) were prepared in acetic acid-urea buffer containing glycerol and naphthol red as a tracking dye. Electrophoresis was at a constant current of 2.5 mA/tube gel. The proteins were run toward the cathode for approximately 2 h, until the 100 µg of cytochrome c standard (a brown band) was at the bottom of its tube. Staining and destaining were accomplished as described for SDS-PAGE.

Capillary zone electrophoresis on the three heparin lyases used a Dionex Capillary Electrophoresis System on a 375 µm×70-cm capillary by a previously published method for protein analysis (23) in 20 mM CAPS containing 10 mM potassium chloride, pH 11.0, at 20 kV at room temperature and detection was by absorbance at 280 nm. Heparin lyase I-III samples (20 nl), each containing 2.74, 2.07, and 2.45 mg/ml, respectively, were analyzed.

Mass spectrometry

Heparinases was purified as described by Sasisekharan, et al. *Proc. Natl. Acad. Sci. U.S.A.* 90, 3660–3664 (1993), the teachings of which are incorporated herein and as summarized above. They were extensively desalted using a Centricon P-30 (molecular weight cut-off of 30 kDa) (Amicon, Mass.) and the purity of the peak was determined by high pressure liquid chromatography using a Vydac $C_{18}$ reverse-phase column in a HP 1090 (Hewlett Packard, California), with diode array detection, in a gradient of 0 to 80% acetonitrile in 0.1% TFA for 60 min. Protein was monitored at 210 and 277 nm. Heparinase I, II and III were collected in a microfuge tube and lyophilized (VirTis Freeze Mobil Model 12, VirTis Inc., New York). Protein concentration was determined by use of the Micro BCA reagent (Pierce Inc., Illinois) relative to a bovine serum albumin standard.

Mass spectrometry was performed on the heparinase preparations to determine purity, homogeneity and molecular mass. About 2 µg of heparinase were mixed with 1 µl of 10 mg/ml sinapinic acid (in 80% acetonitrile 0.1% TFA in water), in equal vol./vol. ratio and then analyzed using laser desorption mass spectrometry (Laser MAT, Finnigan, Calif.). The results demonstrate the purity, homogeneity, and expected molecular mass.

II. Assays for determining effectiveness and effective concentration of angiogenesis inhibitors in vivo Assays were used to test heparinase for endothelial cell proliferation, FGF binding to endothelial cell receptors, and inhibition of angiogenesis in vivo.

The essential elements of these assays include using endothelial cells as the assay target and stimulation of the endothelial cells with known angiogenesis factors to compare a putative inhibitor's effect in unstimulated, as compared to stimulated, endothelial cells. Endothelial cells that can be used include capillary endothelial cells and umbilical vein endothelial cells. Factors which can be used to stimulate the endothelial cells include acidic or basic fibroblast growth factor.

The following assays are based on assays described in the prior art that have been modified for the purpose of screening heparinase for inhibition of angiogenesis in vivo.

EXAMPLE 1

Effect of heparinase in the Chick chorioallantoic membrane bioassay

The chick chorioallantoic membrane assay (CAM), described by Taylor and Folkman, *Nature* (London) 297, 307–312 (1982), is used to determine whether the compound is capable of inhibiting neovascularization in vivo. The effect of the compound on growing embryonic vessels is studied using chick embryos in which capillaries appear in the yolk sac at 48 h and grow rapidly over the next 6–8 days.

On day 3 of development, fertilized chick embryos are removed from their shells and placed in plastic petri dishes (1005, Falcon). They are maintained in humidified 5% $CO_2$ at 37° C. On day 6, 4 µg samples of purified heparinases are mixed in methylcellulose disks and applied to the surfaces of the growing CAMs above the dense subectodermal plexus. Following a 48 hour exposure of the CAMs to heparinases, avascular zones, free of capillaries and small vessels are observed using a binocular dissecting microscope at $\times 7^{-10}$ magnification.

Tissue specimens are fixed in formalin at room temperature and rinsed in 0.1M cacodylate buffer pH 7.4. The specimens are embedded in JB-4 plastic (Polysciences) at 4° C. and 3 µm sections are cut using a Reichert 2050 microtome. Sections are stained with toluidine blue and micrographs taken on a Zeiss photomicroscope using Kodak TM×100 and a green filter.

Figure 1A:
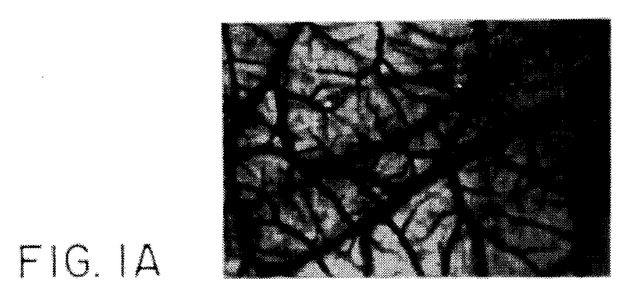
FIG. 1a is the CAM with heparinase I containing disk: 100% of the eggs tested (n=12) of several different batches of heparinase I, had avascular zones.
Figure 1B:
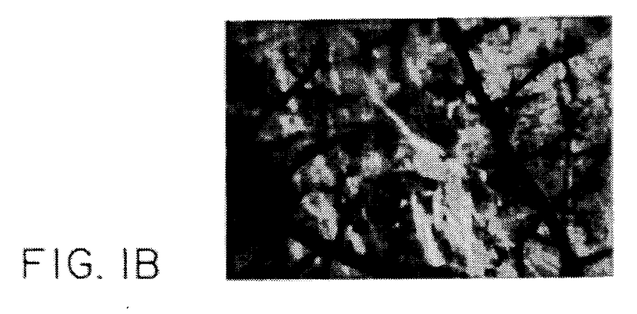
FIG. 1b is a normal CAM containing an empty methylcellulose disk.
Figure 1C:
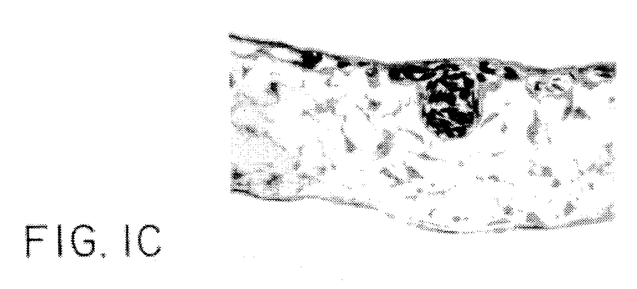
FIG. 1c are histological sections of day 8 normal CAMs ×800.
Figure 1D:
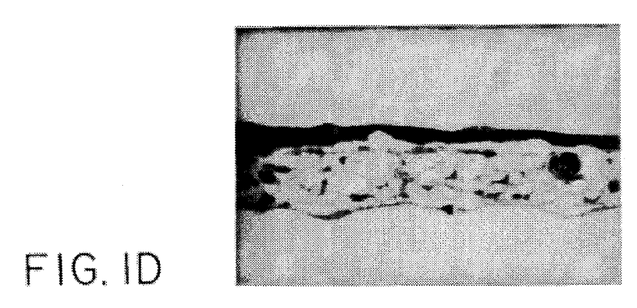
FIG. 1d heparinase I treated CAM.
Figure 2:
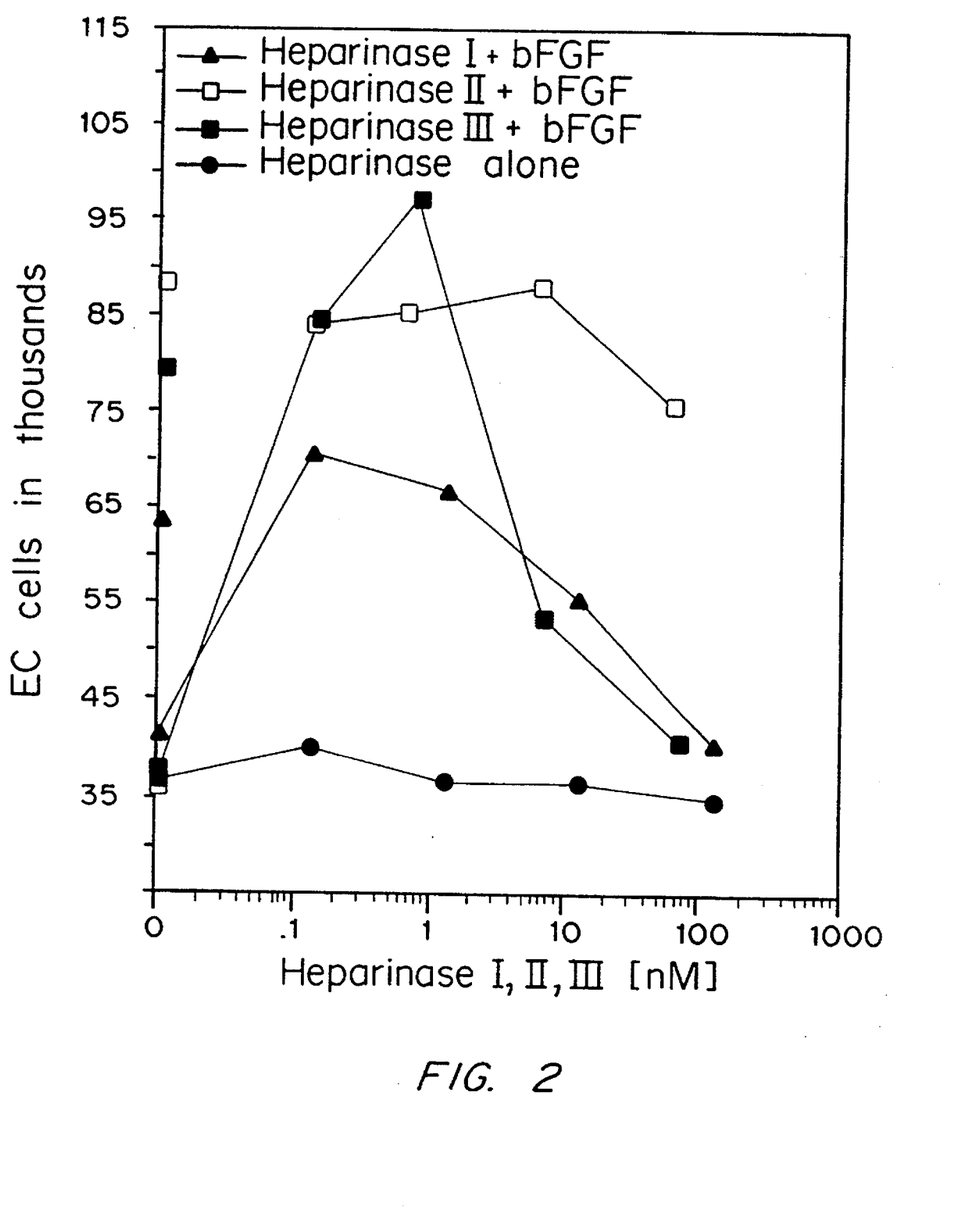
FIG. 2 is a graph of capillary endothelial cells growth ($10^3$) versus heparinase concentration (μg/ml), in the presence (open triangles) or absence (X) of FGF.

The results are shown in FIG. 1a, 1b, 1c, and 1d for heparinase I. On day 6, heparinase I (100 pmoles) was mixed in methylcellulose disks and applied to the surfaces of the growing CAMs above the dense sub-ectodermal plexus. FIG. 1a is a photograph of the CAM with heparinase I containing disk injected with India ink: 100% of the eggs tested (n=12) of several different batches of heparinase I had avascular zones; FIG. 1b is a normal control CAM containing an empty methylcellulose disk; FIG. 1c is a histological section of a day 8 normal CAM ×800; and FIG. 1d is a histological section of a heparinase I treated CAM. The data for heparinase III was similar.

Purified samples of heparinases I and III (100 and 50 pmole respectively) in methylcellulose discs caused 100% inhibition of embryonic neovascularization, resulting in large avascular zones, as shown in FIG. 1a. In contrast, heparinase II (50 pmole) and control CAMs implanted with empty methylcellulose discs did not develop avascular zones, as shown by FIG. 1b. Histological analysis of heparinase I treated CAM revealed a mesoderm that was thinner than normal, containing dividing fibroblasts and nearly no capillary endothelial cells, as shown by FIG. 1c and d.

EXAMPLE 2

Assay for Inhibition of capillary endothelial cell proliferation

Capillary EC proliferation in response to an angiogenic stimulus is a critical component of neovascularization, as discussed by Ausprunk and Folkman, *J. Microvasc. Res.* 14, 153–65 (1977). By utilizing the specific cells involved in angiogenesis, and stimulating them with known angiogenesis factors, in this case basic fibroblast growth factor (bFGF), as reported by D'Amore and Klagsbrun, *J. Cell Biol.* 99, 1545–1549 (1984), it is possible to mimic the angiogenesis process in vitro. This type of assay is the assay of choice to demonstrate the stimulation of capillary EC proliferation by various angiogenic factors and inhibitors, as reviewed by Shing, et al., *Science* 223, 1296–1298 (1984).

Capillary EC were stimulated to proliferate by basic fibroblast growth factor (bFGF), a known angiogenic molecule, and then challenged with varying concentrations of heparinase. Following a three day incubation period, the number of endothelial cells was measured by electronic cell counting. Two concentrations of bFGF were used in the assay and a control was performed, where the effect of heparinase in the absence of bFGF was also investigated.

Capillary ECs were plated in DME/5 onto gelatin-coated (1.5% gelatin, wt/vol [Difco, Detroit, Mich.] 24-well tissue culture dishes (nunc, Roskilde, Denmark). At the indicated times, inhibitor samples and acidic FGF (aFGF) (F.G.F. Co., La Jolla, Calif.) were added to some of the wells. Wells containing PBS alone and PBS and aFGF were included as controls. These substances were added simultaneously in volumes that did not exceed 10% of the final volume. After incubation with the test substances for the designated times, medium was aspirated, cells were washed with 0.5 ml of PBS, removed by trypsinization (0.5 ml 0.05% trypsin-0.02% EDTA; Gibco Laboratories), and counted electronically with a cell counter (Coulter Electronics, Hialeah, Fla.)

This cell counting assay was supported by an additional proliferation assay which measures the number of endothelial cells in culture on the basis of the colorimetric measurement of cellular acid phosphatase.

As seen from FIG. 1 and Table 1, heparinase I is a potent inhibitor of bFGF-stimulated capillary EC proliferation. Capillary EC proliferation (upon stimulation by bFGF) measurement indicated that heparinase, at a 100 nM concentration, caused 100% inhibition of proliferation. On the other hand, at low heparinase concentration (300 pM), there was potentiation of bFGF mediated ECM proliferation by about 30%. Heparinase alone (in the absence of bFGF) has only an inhibitory effect on the EC growth and causes about 25% inhibition at a 100 pM concentration.

Heparinase III is also a potent inhibitor of bFGF-stimulated capillary EC proliferation. In fact, heparinase III seems more potent than heparinase I. At a concentration of approximately 70 nM, it is 100% inhibitory of the EC proliferation. Heparinase III also seems different than that of heparinase I, in action, due to the fact at low heparinase III concentrations (200 pM), there is a proliferation of EC of about 45%.

Heparinase II is marginally inhibitory. It does not have significant potentiating properties at concentrations similar to the concentrations at which heparinase I or III are inhibitory.

TABLE 1

| Capillary Endothelial Cell Proliferation Assay demonstrating the Effect of heparinases. | | | | |
|---|---|---|---|---|
| Enzyme | 0.005 µg/ml | 0.05 µg/ml | 0.5 µg/ml | 5.0 µg/ml |
| Heparinase I | +12% | no effect | −25% | −100% |
| Heparinase II | −4% | −8% | no effect | −20% |
| Heparinase III | +12% | +45% | −60% | −95% |

EXAMPLE 3

Effect of heparinase on confluent BCE cells

The results in examples 1 and 2 suggested that the effects of heparinases I and III on neovascularization in vivo, and BCE proliferation in vitro, reflect their ability to interfere with the action of bFGF. It is known that heparan sulfate (as a low affinity receptor) is essential for bFGF receptor (high affinity receptor) binding and activity, as reviewed by Klagsbrun, M. & Baird, A. *Cell* 67, 229–231 (1991); Baird, A. & Ling, N. *Biochem. Biophy. Res. Commun.* 142, 428–435 (1987); Moscatelli, D. *J. Cell. Physiol.* 131, 123–130 (1987); and Yayon, et al. *Cell* 64, 841–848 (1991), and the degradation of cell surface heparan sulfate with heparinase I results in inhibition of bFGF receptor binding, as reported by Baird, et al., Moscatelli, and Yayon, et al, and Nugent, M. A. & Edleman E. *Biochemistry* 31, 8876–8883 (1992). Furthermore, heparinase III treatment substantially reduced receptor binding, mitogenic activity, and blocked terminal differentiation of MM14 skeletal muscle cells, as reported by Rapraeger, et al. Science 252, 1705–1708 (1991). These results suggest that the heparinases could alter the action of bFGF at the level of receptor binding. Therefore, the effects of heparinases I, II and III treatment on $^{125}$-bFGF receptor binding were investigated.

Methods and Materials

BCEs were treated with the three heparinases for 30 min at 37° C., and then equilibrium binding of $^{125}$I-bFGF to heparan sulfate and bFGF receptors was evaluated.

$^{125}$I-bFGF was prepared by a modification of the Bolton-Hunter procedure (Bashkin, et al., 1989; Kurokawa, et al., 1989). This technique has been demonstrated to produce active $^{125}$I-bFGF as determined by its ability to bind heparin-Sepharose and to stimulate DNA synthesis in Balb/c3T3 and bovine capillary endothelial cells (Bashkin, et al., 1989; Kurokawa, et al., 1989). The specific activity of the $^{125}$I-bFGF was assessed by stimulation of proliferation of Balb/c3T3 cells and was 25–100 µCV/µg.

Confluent capillary EC monolayers were prepared by plating 1×10$^5$ cells per 4 cm$^2$ well (12-well plates, Costar, Cambridge, Mass.) in DMEM, 10% calf serum (1 ml/well) and incubating at 37° C. for 3–5 days. To initiate enzyme treatment, the medium was removed, the cells washed one time with DMEM (1 ml/well), and heparinase added at concentrations of 0, 0.1, 1, 10, or 100 nM in 0.25 ml DMEM containing 5 mg/ml BSA. Enzyme treatment was carried out at 37° C. for 30 min. When treatment was completed the enzyme medium was removed and the monolayers washed twice (1 ml/well/wash) with cold (4° C.) binding buffer (DMEM, 25 mM HEPES, 0.5% gelatin), and then incubated for 10 min at 4° C. in 0.5 ml binding buffer to precool the cells. $^{125}$I-bFGF (5 ng, 0.66 nM, (1.25×10$^5$ to 5×10$^5$ cpm) was then added. The plates were incubated at 4° C. for 2 h, at which point the binding buffer was removed and each well washed 3 times with cold binding buffer (1 ml/well/wash). The amount of a $^{125}$I-bFGF bound to HSPG and receptor was determined sequentially in each culture using a modification of the salt/acid washing technique of Moscatelli, D. *J. Cell. Physiol.* 131, 123–130 (1987) and Nugent, M. A. & Edleman E. *Biochemistry* 31, 8876–8883 (1992). $^{125}$I-bFGF bound to HSPG was released by exposure to high salt buffer (2M NaCl, 20 mM HEPES, pH 7.4; 0.5 ml/well for 5 s), and the $^{125}$I-bFGF bound to receptors was extracted by incubation of the monolayers in low pH buffer (2M NaCl, 20 mM sodium acetate, pH 4.0; 0.5 ml/well; 5 min) followed by a wash with the same buffer (0.5 ml/well). $^{125}$I-bFGF was determined in all samples by counting in a 1272 Clini-Gamma gamma counter (LKB Nuclear, Gaithersburg, Md.). The $^{125}$I-bFGF bound that was not competed by an excess (5 µg; 55 nM) of unlabeled bFGF was defined as nonspecific and was subtracted from the experimental points. The number of cells attached to the culture plates before and after the salt and acid washes was similar.

Figure 3A:
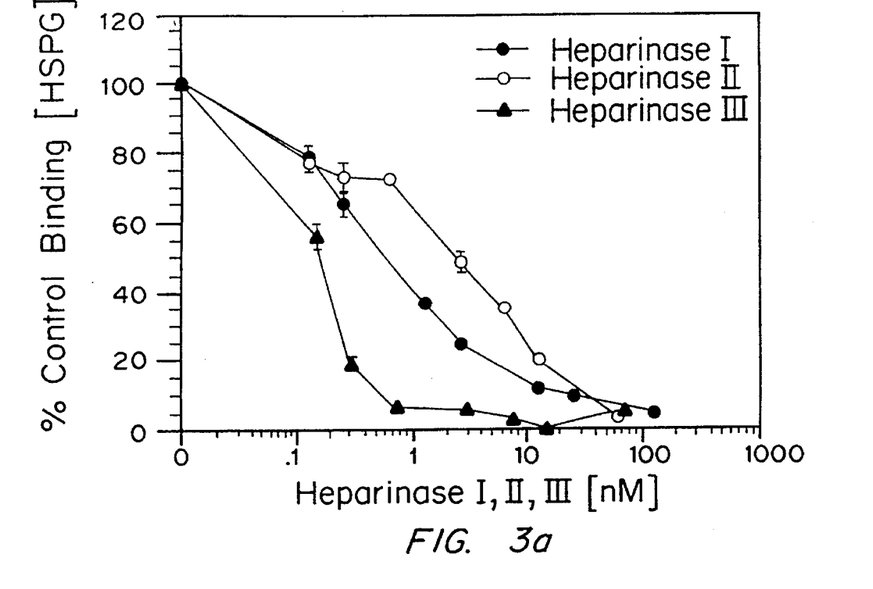
FIG. 3a and 3b are graphs of the percent control of HSPG (a) or bFGF (b) binding to bovine capillary endothelial (BCE) cells versus heparinase (nM).

Results $^{125}$I-bFGF binding to heparan sulfate proteoglycan (HSPG) and cell surface receptor on confluent capillary ECs treated with heparinases I, II and III in concentrations of 0.1, 1, 10, and 100 nM was performed. Binding of FGF to HSPG indicates lower affinity receptors; binding of FGF to the receptors indicates high affinity receptors. The results are shown in FIG. 3a. The control binding level (100%) was 1592±69 cpm for HSPG, and 821±27 cpm for receptors. Similar results were observed in five separate experiments. Heparinase treatment did not result in any change in cell viability, as determined by trypan blue exclusion.

It was found that heparinase treatment of capillary EC caused a significant loss in bFGF binding capacity in these cells (FIG. 3a). Treatment with 125 nM heparinase I resulted in greater that 95% loss in HSPG binding sites on ECs accompanied by an over 80% decrease in receptor binding. The half maximal concentrations required to remove HSPG sites and reduce receptor binding were 0.7 nM and 1.5 nM respectively. The dose response for heparinase-induced inhibition of bFGF mitogenesis and bFGF receptor binding are similar, suggesting that these two activities may be related.

$^{125}$I-bFGF$^1$ (5 ng, 0.55 nM, (1.25-5)×10$^5$ cpm) was added directly to each well containing platelets. The platelets were incubated at 4° C. for 2 hours, at which point the binding buffer was removed and each well washed 3 times with cold binding buffer (1 ml/well per wash). The amount of $^{125}$I-bFGF bound to HSPG and CSR was determined sequentially in each culture using a modification of the salt/acid washing technique (Moscatelli, 1987; Nugent and Edelman, 1992). The $^{125}$I- bFGF bound to HSPG was released by exposure to high salt buffer (2M NaCl, 20 mM HEPES, pH 7.4; 0.5 ml/well for 5 seconds), and then the CSR bound $^{125}$I-bFGF was extracted by incubation of the monolayers in low pH buffer (2M NaCl, 20 mM Sodium Acetate, pH4.0:0.5 ml/well; 5 min) followed by a wash with the same buffer (0.5 ml/well). $^{125}$I-bFGF was determined in all samples by counting in a 1272 CliniGamma gamma counter (LKB Nuclear, Gaithersburg, Md.). The $^{125}$I-bFGF bound that was not competed by an excess (5 µg; 555 nM) of unlabeled bFGF was defined as nonspecific and was subtracted from the experimental points. The number of cells attached to the culture plates before and after the salt and acid washes was not different.

Figure 3B:
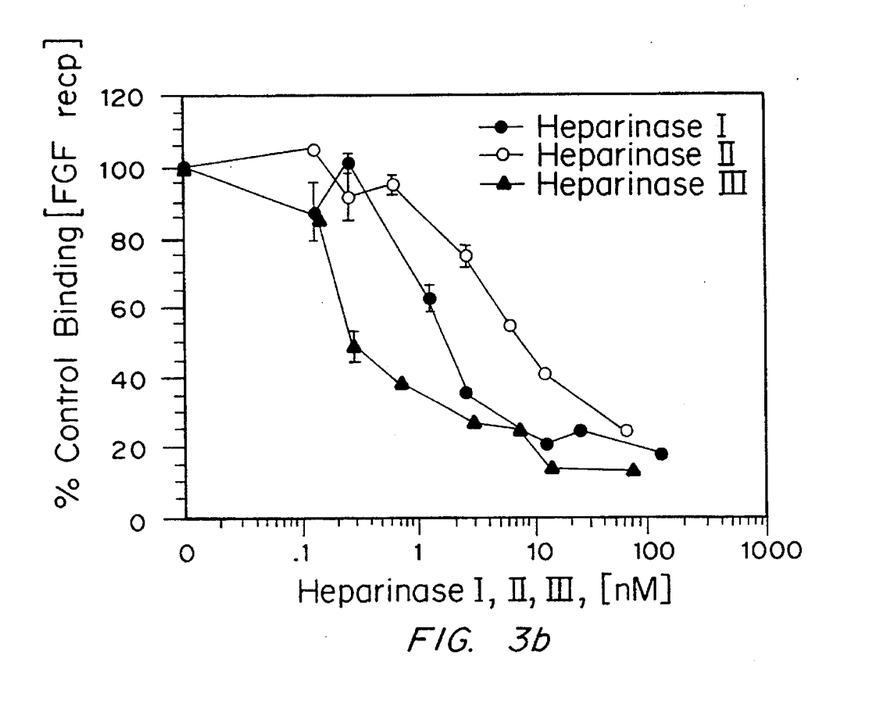

Heparinase treatment of BCEs decreased bFGF binding to these cells in a dose-dependent fashion, as shown in FIG. 3b. There was not only a significant loss of bFGF binding, but also a dramatic difference in the effects of the three heparinases. The concentrations of heparinase I required to reduce bFGF binding to heparan sulfate and receptor sites by 50% were 0.5 nM and 1.5 nM, respectively. For heparinase II, IC$_{50}$ concentrations were 2 nM and 8 nM, respectively, for the heparan sulfate and the receptor binding sites. On the other hand, heparinase III was most potent in inhibiting the bFGF binding, with an IC$_{50}$ of 0.15 nM and 0.2 nM for the heparan sulfate and the receptor binding, respectively. Heparinase III potency is an order of magnitude greater than that of heparinase II; this could be due to slower kinetics of heparinase II compared to those of heparinase III. In the concentration range where potentiation of BCE proliferation by heparinases III and I occurs, between 0.1 and 1 nM, bFGF binding to the cell surface heparan sulfate is eliminated by greater than 80% for heparinase III, and by approximately 60% for heparinase I; the receptor binding is eliminated by only 50% for heparinase III and by approximately 20% for heparinase I. For the same concentration range of heparinase II, 0.1 to 1 nM, about 25% heparan sulfate binding sites and about 10% of the receptor binding are eliminated; heparinase II inhibition of BCE proliferation is about 6%.

While heparinase II has a marginal effect on the BCE proliferation in the concentration ranges of between 10 and 100 nM where heparinase III and I dramatically inhibit BCE proliferation, all three enzymes show similar effects in bFGF binding to these cells. In the 10 to 100 nM concentration range, almost all heparan sulfate binding and about 90, 85 and 80% of the receptor binding is eliminated for heparinases III, I and II, respectively.

In summary, the effect of heparinase was first tested on the proliferation of capillary endothelial cells (ECs) in vitro in the presence and absence of bFGF, a potent stimulator of EC proliferation and angiogenesis. Heparinase I was a powerful inhibitor of FGF-stimulated capillary EC proliferation with an $IC_{50}$ of 60 nM. At very low concentrations of heparinase (14.2 pM and 142 pM) this enzyme caused small but reproducible potentiation of FGF stimulation.

To determine the cell specificity of heparinase's anti-proliferative effect, it was tested against bovine aortic endothelial cells, bovine aortic smooth muscle cells (SMCs) and Balb/c 3T3 cells. Heparinase did not inhibit the proliferation of any of these cell types even at twice the $IC_{50}$ concentration for capillary EC. Heparinase II potentiated SMC proliferation in the presence of platelet derived growth factor (PDGF); heparinase I had no effect while heparinase III had marginal effect in the potentiation of SMC proliferation in the presence of PDGF. PDGF is the mitogen of choice for stimulation of proliferation of smooth muscle cells.

Basic fibroblast growth factor (bFGF) is a potent mitogen for bovine capillary endothelial cells (BCEs) and is considered an important mediator of neovascularization. The three heparinases were tested for their effect on BCE proliferation in vitro in the presence and absence of bFGF. Heparinases I and III at $IC_{50}$ of 21 nM and 6 nM, respectively, significantly inhibited bFGF-stimulated BCE proliferation, as shown in FIG. 3b. It should be noted that, in the presence of bFGF, heparinases I and III potentiated BCE proliferation in very low concentration ranges (0.1 nM to 1 nM). While heparinase I potentiated up to about 20% and heparinase III potentiated up to approximately 40%, heparinase II did not have any potentiating effect, and its inhibition of the bFGF mediated proliferation was marginal (approximately 20% at 100 nM concentration). The anti-proliferative effect of heparinases I and III appears specific to BCE, in that these heparinases did not inhibit the proliferation of bovine aortic smooth muscle cells or NIH 3T3 cells (with bFGF as the mitogen), even when tested at twice the concentration of heparinase in the same assay.

Preparation of Pharmaceutical Compositions

As noted above, several types of heparinase can be used as described herein to inhibit angiogenesis. The effective dosage will depend on the purity and origin of the heparinase, as well as the type, for example, heparinase I versus heparinase II. The preferred enzymes are heparinase I and heparinase III from F. *heparinum*. Pharmaceutical compositions are prepared using heparinase as the active agent to inhibit angiogenesis based on the specific application. Application is either topical or localized. For topical application, the purified heparinase is combined with a carrier so that an effective dosage is delivered, based on the desired activity, i.e. ranging from an effective dosage, for example, of 1 and 4 µg heparinase (with 100% inhibition of angiogenesis at between 3 and 4 µg) to prevent localized angiogenesis to between 10 and 100 nM to inhibit capillary endothelial cell proliferation, with 100% inhibition at approximately 80 nM heparinase I or III. A topical heparinase composition is applied to the skin for treatment of diseases such as psoriasis. The carrier may be in the form of an ointment, cream, gel, paste, foam, aerosol, suppository, pad or gelled stick.

A topical heparinase composition for treatment of some of the eye disorders discussed above consists of an effective amount of heparinase in an acceptable ophthalmic excipient such as buffered saline, mineral oil, vegetable oils such as corn or arachis oil, petroleum jelly, Miglyol 182, alcohol solutions, or liposomes or liposome-like products. Any of these compositions may also include preservatives, antioxidants, antibiotics, immunosuppressants, and other biologically or pharmaceutically effective agents which do not exert a detrimental effect on the heparinase.

Heparinase compositions for local or regional administration, for example, into a tumor, will generally include an inert diluent, and will be administered in an amount effective to inhibit angiogenesis, as noted above. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. Commercially available heparinase preparation come either lyophilized or in sterile water or buffer, but are rarely of the purity that is desired for this application.

For directed internal topical applications, for example for treatment of ulcers or hemorrhoids, or other lesions of mucosal membranes, the heparinase composition may be in the form of tablets or capsules, which can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

In a preferred form, the heparinase is administered in combination with a biodegradable, biocompatible polymeric implant which releases the heparinase over a controlled period of time at a selected site. Examples of preferred polymeric materials include polyanhydrides, polyorthoesters, polyglycolic acid, polylactic acid, polyethylene vinyl acetate, and copolymers and blends thereof, and gels formed of materials such as a polysaccharide such as alginate or heparin, which is bound by heparinase in the absence of calcium. In the latter case, the heparinase is released under physiological conditions. Heparinase can also be administered at a local site by infusion pump, for example, of the type used for delivering insulin or chemotherapy to specific organs or tumors.

Modifications and variations of the compositions of the present invention, and methods for use, will be obvious to those skilled in the art from the foregoing detailed description. Such modifications and variations are intended to fall within the scope of the appended claims.

We claim:

1. A composition inhibiting angiogenesis comprising an effective amount of a heparinase selected from the group consisting of heparinase I and heparinase III from *Flavobacterium heparinum* in a pharmaceutically acceptable carrier for topical administration to inhibit angiogenesis at a selected site in a non-heparinized patient in need of treatment thereof, wherein the carrier delivers to a site where angiogenesis is to be inhibited between approximately one and four µg heparinase or a concentration of between 10 and 100 nM heparinase.

2. The composition of claim 1 wherein the heparinase is in an acceptable ophthalmic carrier.

3. The composition of claim 1 wherein the heparinase is in a pharmaceutically acceptable carrier for topical application to the skin.

4. The composition of claim 1 wherein the heparinase is in a biodegradable, biocompatible polymeric delivery device.

5. A method for inhibiting angiogenesis comprising: administering to a non-heparinized patient in need of treatment thereof to inhibit angiogenesis an effective amount of a heparinase selected from the group consisting of heparinase I and heparinase III from *Flavobacterium heparinum* in a pharmaceutically acceptable carrier to a site where inhibition of angiogenesis is desired.

6. The method of claim 5 wherein the site is a tumor.

7. The method of claim 5 further comprising administering the heparinase topically in a pharmaceutical vehicle suitable for topical application.

8. The method of claim 5 further comprising providing the heparinase in a biodegradable, biocompatible polymeric delivery device.

9. The method of claim 5 further comprising providing the heparinase in a pharmaceutically acceptable vehicle for injection.

10. The method of claim 5 further comprising administering the heparinase in a pharmaceutically acceptable vehicle for topical application to the eye.

11. The method of claim 5 wherein an effective dose at the site where angiogenesis is to be inhibited is between approximately one and four µg heparinase or a concentration of between 10 and 100 nM heparinase.

12. The method of claim 5 wherein the effective dose is a dose effective in diminishing the symptoms of psoriasis.

13. The method of claim 5 wherein the effective dose is a dose effective in diminishing the number of blood vessels growing into a tumor.

14. The method of claim 5 wherein the effective dose is a dose effective in diminishing the symptoms of eye diseases characterized by abnormal neovascularization.

* * * * *